United States Patent
Rozov et al.

(10) Patent No.: US 6,800,786 B1
(45) Date of Patent: Oct. 5, 2004

(54) PREPARATION OF DESFLURANE

(75) Inventors: Leonid A. Rozov, Fair Lawn, NJ (US); Ralph A. Lessor, New Providence, NJ (US)

(73) Assignee: Baxter International, Inc., Deerfield, IL (US)

(*) Notice: Subject to any disclaimer, the term of this patent is extended or adjusted under 35 U.S.C. 154(b) by 0 days.

(21) Appl. No.: 10/645,884

(22) Filed: Aug. 21, 2003

Related U.S. Application Data

(60) Provisional application No. 60/413,382, filed on Sep. 25, 2002.

(51) Int. Cl.$^7$ ............................................. C07C 41/22
(52) U.S. Cl. ............................................. 568/683
(58) Field of Search ........................................... 568/683

(56) References Cited

U.S. PATENT DOCUMENTS

| | | |
|---|---|---|
| 3,897,502 A | 7/1975 | Russell et al. |
| 4,855,511 A | 8/1989 | Halpern et al. |
| 4,874,901 A | 10/1989 | Halpern et al. |
| 4,888,139 A | 12/1989 | Halpern et al. |
| 5,015,781 A | 5/1991 | Robin et al. |
| 5,026,924 A | 6/1991 | Cicco |
| 5,205,914 A | 4/1993 | Rozov et al. |
| 6,225,511 B1 | 5/2001 | Chambers et al. |

FOREIGN PATENT DOCUMENTS

| | | |
|---|---|---|
| DE | 2361058 | 6/1975 |
| GB | 2 219 292 A | 12/1989 |
| JP | 06192154 | 7/1994 |
| WO | WO 94/08929 | 4/1994 |

*Primary Examiner*—Rosalynd Keys
(74) *Attorney, Agent, or Firm*—Dechert LLP

(57) ABSTRACT

Provided is a method for the preparation of desflurane wherein isoflurane is reacted with 0.7–1.2 mol. % of antimony pentachloride and 1.3–2.2 molar equivalents of hydrogen fluoride. Typically, the method is conducted by addition of hydrogen fluoride to a mixture of isoflurane and antimony pentachloride. After the addition of hydrogen fluoride is completed, the reaction is preferably maintained at temperatures of about 9–18° C. for about 6 to 7 hours, before being quenched.

5 Claims, 5 Drawing Sheets

PREPARATION OF DESFLURANE

This application claims the priority of US Provisional Application 60/413,382 filed Sep. 25, 2002, the disclosure of which is hereby incorporated by reference as if fully set forth herein.

The present invention relates to a process for preparing the inhalation anesthetic 1,2,2,2-tetrafluoroethyl difluoromethyl ether (also known as desflurane).

Desflurane is one of the most effective and widely used inhalation anesthetics currently available on the market. As such, there is considerable interest in developing improved synthetic routes that are practical to implement on commercial scales. One commercial process for the synthesis of desflurane disclosed in U.S. Pat. No. 5,026,924, herein incorporated by reference, relates to a process for preparing desflurane from the intermediate isoflurane, (1-chloro-2,2,2-trifluoroethyl difluoromethyl ether) by treatment with hydrogen fluoride in the presence of antimony pentachloride, alone or in combination with antimony trichloride according to reaction (1).

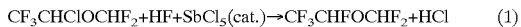

$$CF_3CHClOCHF_2 + HF + SbCl_5(cat.) \rightarrow CF_3CHFOCHF_2 + HCl \quad (1)$$

While reaction (1) serves as a basis for a successful commercial route for desflurane, a drawback associated with its use is the generation of by-products in addition to desflurane. A major proportion of these by-products is bis-1,2,2,2-tetrafluoroethyl ether, whose formation is undesirable in at least two aspects. In one aspect, the formation of this by-product is achieved at the expense of isoflurane consumed and desflurane produced. The formation of the by-product therefore lowers the overall recovery of the reaction. In a second aspect, the formation of the by-product also increases the complexity of the subsequent purification of desflurane. Bis-1,2,2,2-tetrafluoroethyl ether exists as a mixture of two stereoisomers whose boiling points (37° C. and 49° C.) are similar to those of desflurane (b.p. 23.5° C.) and isoflurane (b.p. 48.5° C.) and therefore, multiple distillations stages are almost invariably needed to separate the two stereoisomers of this impurity from useful materials. Moreover, distillation fractions containing the by-products often contain substantial quantities (e.g., >99 percent by weight) of desflurane. Due to the fact that additional separations of the contaminated fractions are unfavorable from the standpoint of economics, these fractions are typically discarded, lowering the isolated yield of the purified desflurane product. Accordingly, it is advantageous to adjust the reaction conditions for reaction (1) to minimize the levels of by-products present in the crude reaction product.

Further optimization of processes based on reaction (1) is also desirable from the standpoint of reducing the levels of hazardous waste streams that are associated with the process. For example, minimizing the quantity of antimony pentachloride that is used decreases the associated volume of water containing the spent catalyst, as aqueous waste streams containing antimony salts are burdensome to treat and costly to dispose of.

Accordingly, alternative cost-effective and efficient methods of preparing desflurane based on reaction (1) are needed. In addition, these methods are preferably more favorable from the standpoint of reduced volumes of hazardous waste streams and reduced environmental impact.

SUMMARY OF THE INVENTION

In one embodiment, the invention relates to a method for the preparation of desflurane wherein isoflurane is reacted with 0.7–1.2 mol. % of antimony pentachloride and 1.3–2.2 molar equivalents of hydrogen fluoride. Typically, the method is conducted by addition of hydrogen fluoride to a mixture of isoflurane and antimony pentachloride. After the addition of hydrogen fluoride is completed, the reaction is preferably maintained at temperatures of about 9–18° C. for about 6 to 7 hours, before being quenched.

DEFINITIONS

Figure 1:
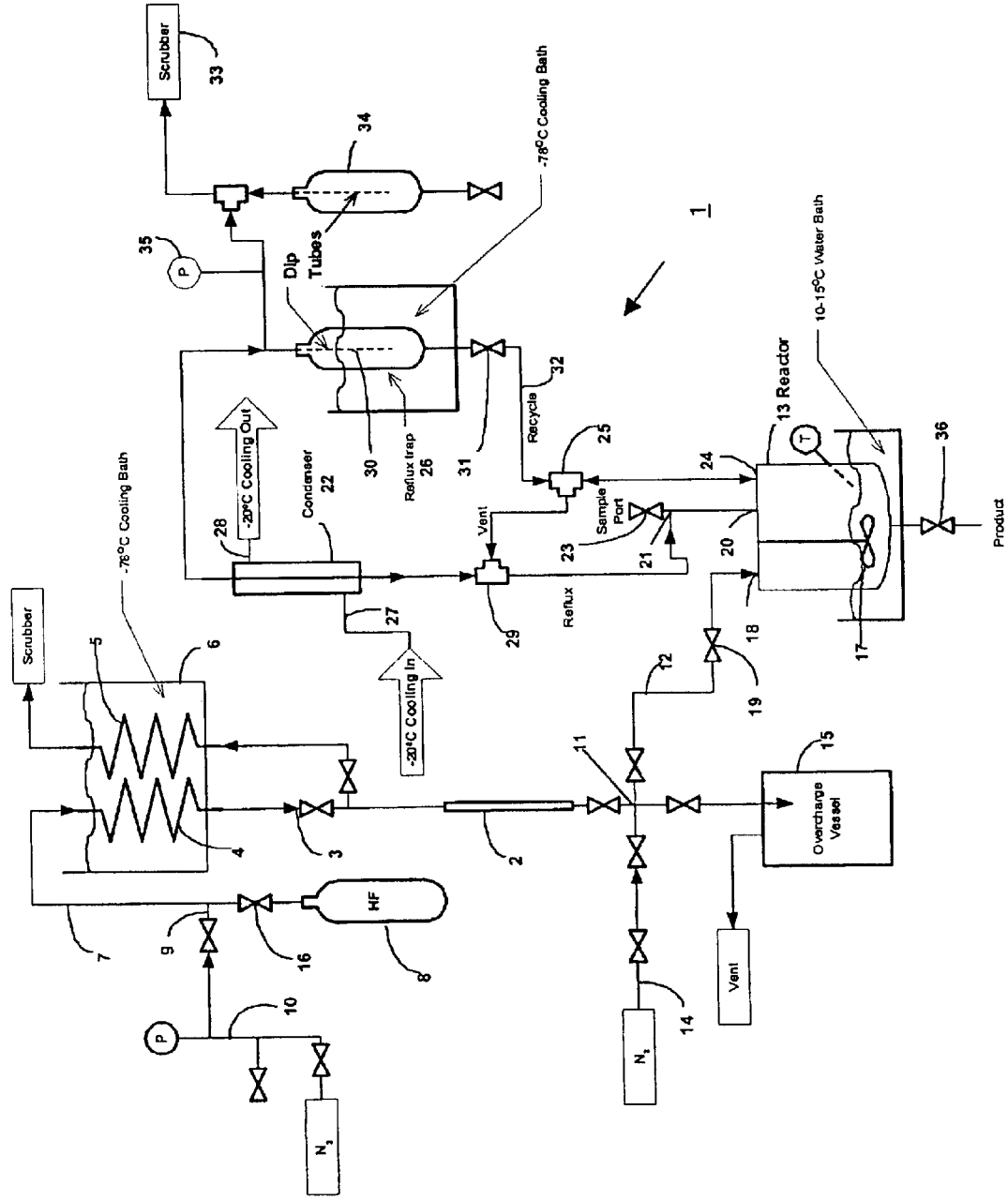
FIG. 1 displays a laboratory scale fluorination (1) apparatus useful for practicing the method of the invention.

The following terms shall have, for the purposes of this application, the respective meanings set forth below.

"Molar Equivalents" shall be calculated based on the number of moles of the reagent (e.g., hydrogen fluoride) used per mole of isoflurane charged in the reaction.

"Mole Percent" (or "mol. %") shall mean:

$$\frac{\text{moles of reagent (e.g., } SbCl_5)}{\text{moles of isoflurane charged}} \times 100$$

"Percent Conversion" shall mean:

$$\frac{\text{moles of product obtained}}{\text{moles of isoflurane charged}} \times 100$$

"Percent Recovery" shall mean:

$$\frac{\text{moles of isoflurane} + \text{moles of product obtained}}{\text{moles of isoflurane charged}} \times 100$$

"Weight Percent (or wt. %) of catalyst shall mean:

$$\frac{\text{weight of antimony pentachloride}}{\text{total weight of the reaction mixture}} \times 100$$

"Yield" shall mean:

$$\frac{\text{moles of product obtained}}{\text{moles of isoflurane consumed}} \times 100$$

DETAILED DESCRIPTION OF THE INVENTION

The method of the current invention defines a combination of parameter ranges for reaction (1) that simultaneously provide a substantial increase in the conversion and yield of desflurane, and a substantial decrease in the amount of by-products contained in the crude reaction product over methods conducted with parameters that are outside the defined ranges. The improvements in the reaction performance are surprising in view of the consistently poorer recoveries, yields or conversions that result from simple parametric modifications of the previously detailed reaction conditions. In particular, the method describes a preparation of desflurane using a method that uses an optimized amount of antimony pentachloride in combination with an optimized amount of hydrogen fluoride. The method of the invention decreases the loss of isoflurane and desflurane caused by side reactions, and reduces the level of by-products formed in the method. As a result, the method maintains or improves the overall recovery of economically valuable materials, i.e., desflurane and isoflurane, and at the same time substantially decreases the amount of hazardous waste.

In a general description of the method of the invention, the reaction is typically conducted in a reactor that is initially charged with a mixture of isoflurane and antimony pentachloride, preferably in an inert atmosphere such as a nitrogen atmosphere. Preferably, the hydrogen fluoride is then added to the mixture of isoflurane and antimony pentachloride. The reaction is preferably conducted in the substantial absence of additional solvents, to minimize the burden of the product isolation steps and minimize the volumes of reaction waste streams. In addition, the reaction is preferably run in a manner which permits the escape of the hydrogen chloride by-product in gaseous form, while substantially retaining unreacted hydrogen fluoride in the reaction vessel. This provision results in a final equilibrium condition in which the desflurane content of the mixture is maximized. Upon completion of the reaction, the crude product is typically isolated by water-workup, and can be further purified by, for example, distillation methods.

The method of the invention preferably uses antimony pentachloride to catalyze the halogen exchange of the isoflurane substrate. Preferably antimony pentachloride is used in the amount of 0.7 to 1.2 mol. % relative to the amount of isoflurane charged in the reaction. Applicants have found that these particular ratios of catalyst to isoflurane balances the preference for high conversion rates, and the desirability for minimizing by-product formation. Lower ratios of antimony pentachloride/isoflurane lead to insufficient conversions, while higher ratios of antimony pentachloride/isoflurane result in increased proportions of by-products formed in the crude reaction mixture. In addition, use of higher ratios results in larger volumes of aqueous waste streams containing the spent catalyst upon workup of the reaction mixture.

The ratio of antimony pentachloride/isoflurane is expressed herein as a mole percentage (mol. %) to reflect a value that is independent of the amount of hydrogen fluoride added to the reaction mixture. Other terms that are also common in the art can, of course, be used to express the relative proportion of antimony pentachloride that is added to the reaction mixture such as the weight percentage ("wt. %") of the antimony pentachloride of the total reaction mixture. The value expressed by the weight percentage of antimony pentachloride in the reaction mixture therefore is, in part, dependent on both the amount of isoflurane and hydrogen fluoride added to the reaction mixture. For example, in reaction mixtures that contain 1.56 molar equivalents of hydrogen fluoride, molar ratios of antimony pentachloride of 0.7 to 1.2 mol. % would correspond to a weight percentages of antimony pentachloride (based on the total weight of the reaction mixture) of 0.96 to 1.64 wt. %.

Using the preferred amounts of antimony pentachloride described above, the proportion of hydrogen fluoride added to the reaction mixture is typically in the range of 1.3 to 2.2 molar equivalents of hydrogen fluoride per mole of isoflurane charged. Preferably, the proportion of hydrogen fluoride added to the reaction mixture is in the range of 1.5 to 2.0 molar equivalents per mole of isoflurane charged. These proportions of hydrogen fluoride, when used in combination with the above-described amounts of antimony pentachloride, assure sufficient proportions of desflurane and minimal proportions of by-products in the crude reaction product. In addition, these proportions provide sufficiently high recoveries, conversions and yields.

In preferred embodiments, the amount of hydrogen fluoride is selected to provide an improvement in the conversion of isoflurane to desflurane of 2% or more, and an improvement in the yield of desflurane of 2% or more over a conversion (herein referred to as a "reference conversion") and a yield (herein referred to as a "reference yield") determined from a reference method. The "reference method" referred to herein is conducted using substantially identical parameters as the inventive method (e.g., scale, reaction time, temperature and pressure) except that the reference method uses about 1.8 mol. % of antimony pentachloride and about 1.9 molar equivalents of hydrogen fluoride.

As was mentioned above, the hydrogen fluoride is typically added to a mixture of the isoflurane and antimony pentachloride. Preferably, the hydrogen fluoride is added as a liquid, as this physical state is convenient for the accurate metering of hydrogen fluoride. The hydrogen fluoride is preferably added at the rate of 0.25 to 1.5 molar equivalents per hour. As the reaction is endothermic, provisions for maintaining the temperature at, for example, about 9 to 18° C., and preferably, 9 to 14° C. are generally used. Preferably, the added hydrogen fluoride is substantially anhydrous, as moisture typically adversely affects the reaction performance.

The method of the invention can be conducted without limitation as to the source of the intermediate, isoflurane. Isoflurane, which is itself an effective inhalation anesthetic, can be prepared, for example, from trifluoroethanol ($CF_3CH_2OH$) and chlorodifluoromethane ($CF_2ClH$) according to reactions (2) and (3), as described in U.S. Pat. No. 3,637,477, which is herein incorporated by reference.

$$CF_3CH_2OH + CF_2ClH + NaOH \rightarrow CF_3CH_2OCHF_2 \quad (2)$$

$$CF_3CH_2OCHF_2 + Cl_2 \rightarrow CF_3CHClOCHF_2 \quad (3)$$

Other methods can, of course, be used to obtain the isoflurane.

In the method of the invention, the pressure of reaction (1) can vary depending upon the construction of the reactor used in the process. For example, Applicants have found that the reaction can be conveniently performed at atmospheric pressure by utilizing reactors that are vented to a scrubber so that pressures inside the reactors do not increase.

The reaction mixture is generally maintained at temperatures of about 5 to 18° C., more preferably at about 9 to 14° C. during the hydrogen fluoride addition and in the post-addition period. Typically, the reaction mixture is maintained at 9 to 18° C., and preferably, 9 to 14° C. for a period of 5 to 8 hours or more, and preferably for about 6 hours after the completion of the hydrogen fluoride addition. Preferably, the reaction is quenched by mixing the reaction medium with an excess of water. Provisions for maintaining the temperature of the reaction mixture are well-known in the art, and include heat exchangers and cooling baths.

The process is conducted in a reaction vessel that is preferably substantially inert to hydrogen fluoride and antimony pentachloride. Teflon® (polytetrafluoroethylene), carbon steel, nickel and copper are examples of suitable construction materials for the reaction vessel. For commercial-scale reactions carbon steel is a preferred construction material for the reactor. As will be apparent to those of ordinary skill in the art, it is generally desirable to equip the reaction vessel with provisions that allow the recovery and return of low boiling components, e.g., desflurane, back to the reaction vessel. For instance, a condenser and/or a reflux trap fitted with a line to return the condensed material back to the reaction vessel can be used.

The following examples further illustrate the present invention, but of course, should not be construed as in any way limiting its scope.

Example 1

Standard Operation Procedure of a Laboratory-Scale Fluorination Apparatus

Description of the Laboratory-Scale Fluorination Apparatus

The fluorination apparatus consisted of three major parts: the HF delivery system, a reactor vessel and the cooling/recovery system (see FIG. 1).

1. HF Delivery System

The HF delivery system included a burette (2) made from 75 cm long×0.8 cm ID transparent poly(tetrafluoroethylene) tube. The maximum capacity of this burette was ~40 mL. It had graduation marks every milliliter and the volume of HF could be measured with a precision of 0.5 mL. A top portion of the burette was connected through a Swage lock® fitting (3) with a 1 meter long×0.5 cm ID copper coil (4) and a vent line (5) also made as a coil. These coils were cooled with a dry ice bath (6). The inlet of the coil was attached by Teflon® tubing (7) to the HF tank (8, maximum capacity 1.6 kg) and also, through a tee-connector (9), with an in-house nitrogen line (10). The Swage lock® cross fitting (11) is attached to a lower port of the burette. This fitting was connected by the Teflon® line (12) to a reactor (13), and also to an in-house nitrogen line (14). The third opening served as a vent and was connected by a stainless steel tube to a Teflon® jar (15), which served as an overcharge vessel. Each of the four lines was equipped with a valve.

In a typical procedure for charging the burette (2), the HF tank (8) was immersed in a hot water bath (~35–40° C.) for 10 min. A tank valve (16) was opened for ~30 sec and the gaseous HF filled all lines and condensed in the copper coil (4), which was cooled to −78° C. by dry ice. After this step, the tank valve was closed and a slight pressure of nitrogen (~2 psi) was applied. As a result, the liquid HF was forced from the coil into the graduated burette (2). Excess HF (beyond the intended charge for the reaction) was removed through an exit line into a Teflon® jar (15) filled with ice/water.

2. Reaction Vessel

The initial series of fluorination reactions was performed at atmospheric pressure in 250-mL Teflon® reactor (13) mounted below the HF burette. This unit, which was equipped with a Teflon® stirring bar (17) and a thermocouple well, had three openings. The first opening (18) was equipped with a ball valve (19) and was connected with the HF burette by the Teflon® tubing (12). It also served as an entry port for the introduction of the starting isoflurane and antimony pentachloride prior to the reaction. To the second opening (20), a Swage lock® tee fitting (21) was attached. The side arm of this fitting is connected to a teflux condenser (22). The tee's upper port was used for the sampling of the reaction mixture. It was topped by a ball valve (23) with an attached rubber septum. When needed, the ball valve was opened and a long needle of a pre-cooled syringe was punched through the septum and was inserted into the reactor. The third opening (24) was also equipped with a tee fitting (25). The side arm of this tee was attached to the condenser. This design helped to prevent the overflow of the condenser. The upper port of this fitting was connected with a reflux trap (26). This line allowed the return of low boiling materials (including HF) from the condenser into the reactor.

In other experiments, the Teflon® reactor was substituted by a 250-mL reactor custom-fabricated from carbon steel SA-516 Gr.70 (Bethlehem/Lukens Steel Co. Coatesville, Pa.), which is a construction material more suitable for use in construction of a commercial-scale reactor. This reactor has a curved bottom and a ball valve (36) to drain the product without opening the reactor. The reactor vessel was fitted with a commercially available reactor head unit with integral stirring shaft, constructed of Inconel (Parr Instrument Company, Moline, Ill.).

3. Cooling/recovery System

The 120-cm long reflux stainless steel tube-in-tube condenser (22) was mounted above the fluorinator. The outer ¾" tube had two openings: the lower opening (27) was connected to the outlet port of the cooling recirculating bath kept at −20° C. and the upper opening (28) was attached to the inlet port of this bath. An inner ¼" tube was attached to an outer tube by a series of Swage lock® fittings. The bottom of the condenser had a tee fitting (29). Both openings of this tee were connected to two exit ports of the Teflon® reactor by clear Teflon® tubing. The exit of the condenser was connected to a dip tube (30) inserted through a tee fitting into an entry port of a reflux trap. This unit made out of a stainless steel 250-mL cylinder was kept cold with dry ice. The bottom port of this trap was connected to the fluorinator. A ball valve (31) installed on a line (32) connecting these two apparatus allowed control of the return of the condensed low boiling materials, which were swept away with the gaseous by-product, hydrogen chloride, back to the reactor. The non-condensed gases, which come out from the top of the reflux trap, are passed through the intermediate vessel (34) and then to a scrubber (33) containing 5% caustic. This stainless steel 1-liter vessel (34) serves as a safety feature (trap) preventing the entry of scrubber caustic into the reaction zone. A pressure gauge (35) was attached to a line between the reflux trap (26) and the intermediate vessel (34).

Standard Operation Procedure of the Laboratory-Scale Fluorination Apparatus

All of the Examples 2–6 used a reaction mixture that was charged with 154.0 g of isoflurane, while amounts of antimony pentachloride and hydrogen fluoride were varied according the amount specified in each of the experiments.

In a typical reaction a mixture of isoflurane (154.0 g, 0.834 mol) and antimony pentachloride [2.0–5.0 g, (6.68–16.69 mmol)] were placed in a reactor at room temperature. Hydrogen fluoride [20.0–26.0 g, (1.0–1.3 mol)] was added as a liquid at atmospheric pressure. The rate of hydrogen fluoride addition was 1.0 mL (in bolus amounts) every 3 min. Immediately after the addition began the evolution of the acidic gases was observed and the temperature of the reaction mixture began to decrease. During the addition period the temperature of the reaction mixture was maintained between 9° C. and 14° C. At the beginning of the HF addition the evolution of gases was very rapid, and was accompanied by a drop in temperature, which necessitated external warming of the reactor to maintain the temperature within the desired range. Toward the end of the addition the rate of gas evolution slowed, and slight reflux of low boiling materials was observed in the Teflon® tube connecting the reactor to the reflux condenser. The reaction mixture was stirred at atmospheric pressure for another 5–8 hours (post-addition period). During this period the evolution of the acidic gases and reflux continued and the temperature in the reactor was maintained between 9° C. and 14° C. The reactor was chilled by ice/water mixture to 2–3° C., opened, and the reaction mixture was quenched by pouring into ice-cold water (200 mL). The resulting organic layer was washed twice with weak caustic (2×200 mL, 4.0 g of 50% NaOH in 100 mL $H_2O$). The weight of the crude product was recorded, and it was analyzed by gas chromatography (GC) using a Shimadzu GC-9A instrument equipped with a flame ionization detector and 15 ft×⅛" OD stainless steel column packed with 25% Carbowax 20M coated on Chromosorb WHP, 80/100 mesh (column temperature=75° C., isothermal, run time=40 min, injector temperature=200° C., detector temperature=250° C.).

Example 2

Reaction Performance under Reference Conditions Described in U.S. Pat. No. 5,026,924

A series of experiments were conducted in a laboratory-scale apparatus to evaluate the reaction performance based on a reference set of conditions. These results provided a backdrop from which to evaluate the reaction performance using the improved conditions of the inventive method. A reference set of conditions are described in Example 1 of U.S. Pat. No. 5,026,924 ("the '924 patent"). Example 1 of the '924 patent was conducted at a pilot plant scale, for example, the amount of the substrate isoflurane charged was 166.4 kg. To provide for a more convenient analysis of the reaction performance of a series of multiple reactions, the scale of the reactions was reduced to accommodate conducting the reactions in a laboratory-scale apparatus at atmospheric pressure.

The set of reaction conditions recited in Example 1 of the '924 patent were scaled down in size to accommodate conducting the reaction in the 250-mL carbon steel reactor described above at atmospheric pressure. The reaction was repeated three times at a scale that used 154.0 g of isoflurane. Table 1 compares the conditions and reaction performance for the laboratory scale runs with the conditions and reaction performance recited in Example 1 of the '924 patent.

There are some differences in the results recited in Example 1 of the '924 patent and in the results obtained with the laboratory carbon steel reactor. For example, the crude product composition for the crude product obtained at laboratory scale was superior to the crude product composition described at the pilot plant scale recited in the '924 patent. For example, a larger percentage of desflurane was obtained, while a smaller percentage of by-products were obtained at the laboratory scale. At the same time, the recovery of the organic products and desflurane yield at the laboratory-scale were 12–14% less than those described in Example 1 of the '924 patent.

While not being bound by theory, it is possible the different results obtained using the laboratory scale apparatus and the results recited in Example 1 of the '924 patent are due to different construction materials used to form the reactors in each case. The pilot plant reactor in the '924 patent was made of stainless steel, while the laboratory scale apparatus was formed from carbon steel. Another possible explanation that may account for the different results were the different reaction pressures: Example 1 of the '924 patent describes a pressure of 1–7 psig while the laboratory scale apparatus was run at atmospheric pressure.

Regardless of the differences in the results, the conditions for the laboratory-scale reactions (referred to as the "reference set of conditions") allowed the evaluation of the reaction performance for conditions that used different proportions of antimony pentachloride and hydrogen fluoride.

Example 3

Effect of Varying Proportions of Antimony Pentachloride on the Reaction Performance Fluorination experiments were conducted in the laboratory-scale Teflon® reactor using different amounts of antimony pentachloride catalyst and maintaining a constant molar ratio of isoflurane/HF. The results of this study are summarized in Table 2.

TABLE 1

| # | Lot | Reagents | | Products | | | Recovery, % | Conversion, % | Yield, % |
|---|---|---|---|---|---|---|---|---|---|
| | | Molar ratio Iso/HF | $SbCl_5$*, Wt. % | Des, % | Iso, % | By-products, % | | | |
| 1 | Ex. 1 of U.S. Pat. No. 5,026,924 | 1:1.9 | 2.31 (1.8) | 80.70 | 15.80 | 3.50 | 92.3 | 78.2 | 90.9 |
| 2 | Lab-Scale Average of three runs | 1:1.9 | 2.31 (1.8) | 96.55 | 2.04 | 1.41 | 78.8 | 77.3 | 78.5 |

*Values in parentheses show the mol. % of $SbCl_5$ catalyst

TABLE 2

| # | Reagents Iso/HF Molar Ratio | SbCl$_5$ mol. % | Des, % | Iso, % | By-products, % | Recovery, % | Conversion, % | Yield, % |
|---|---|---|---|---|---|---|---|---|
| 1 | 1:1.2 | 0.4 | 24.33 | 75.62 | 0.034 | 88.5 | 23.1 | 66.8 |
| 2 | 1:1.2 | 0.8 | 59.06 | 40.82 | 0.114 | 85.9 | 52.7 | 78.9 |
| 3 | 1:1.2 | 1.2 | 73.73 | 25.95 | 0.321 | 84.8 | 64.2 | 80.9 |
| 4 | 1:1.2 | 1.6 | 76.80 | 22.76 | 0.447 | 84.3 | 66.4 | 80.8 |
| 5 | 1:1.2 | 2.0 | 75.61 | 23.95 | 0.436 | 83.5 | 64.8 | 79.7 |
| 6 | 1:1.2 | 2.4 | 77.41 | 22.10 | 0.495 | 85.7 | 68.0 | 82.6 |
| 7 | 1:1.2 | 2.8 | 75.45 | 23.95 | 0.598 | 84.0 | 65.2 | 80.3 |
| 8 | 1:1.2 | 3.2 | 74.29 | 25.06 | 0.644 | 83.2 | 63.7 | 79.1 |

Based on the results in Table 2 two graphs were generated. The first graph (FIG. 2) shows the dependence between the desflurane concentration in the reaction mixture and the mole percentage of antimony pentachloride catalyst used.

Figure 2:
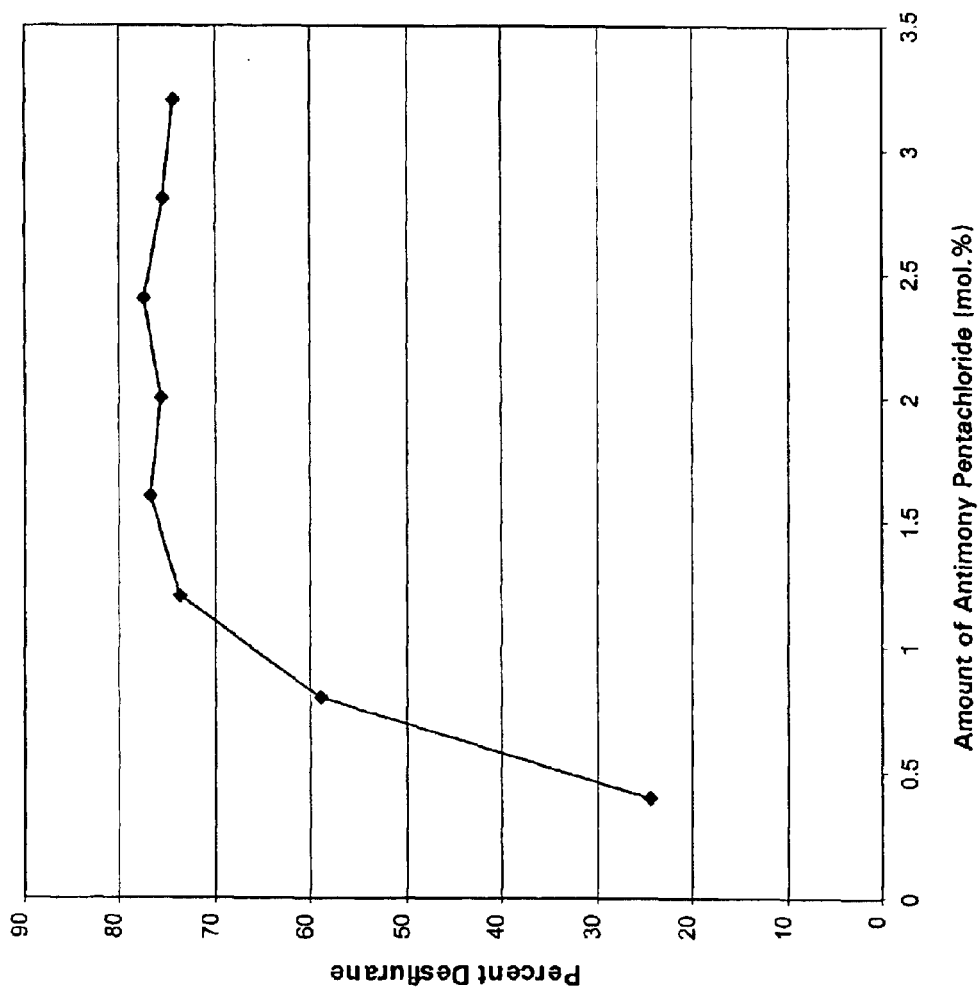
FIG. 2 is a graphical representation of the relationship of the percentage of desflurane present in the crude product and varying amounts of antimony pentachloride (mol. %) at a constant molar ratio of HF:isoflurane=1.2.
Figure 3:
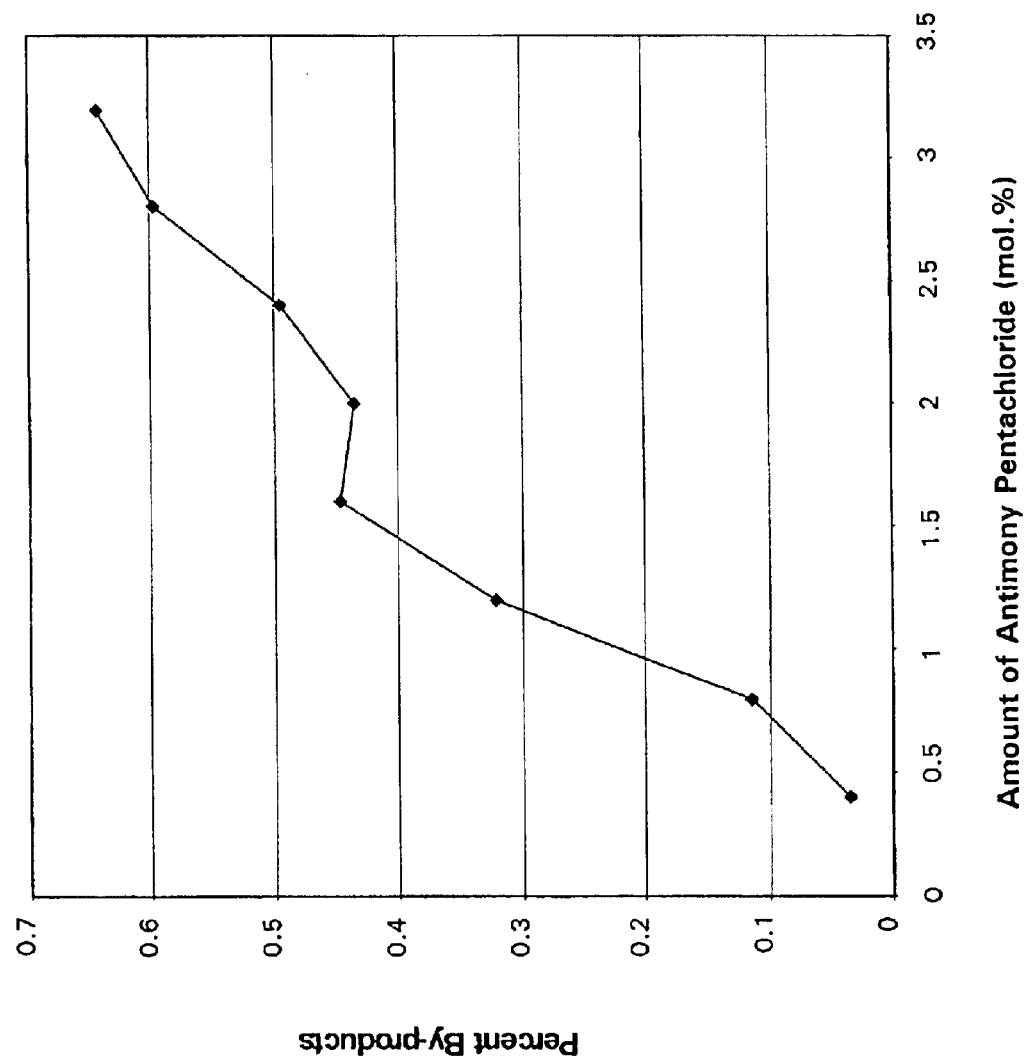
FIG. 3 is a graphical representation of the relationship of the percentage of by-products present in the crude product and varying amounts of antimony pentachloride (mol. %) at a constant molar ratio of HF:isoflurane=1.2.

From Table 2 and also from FIG. 2 it is apparent, that at increased mole percentages of antimony pentachloride, the concentration of desflurane in the crude reaction product remained practically unchanged (see entries 3–8). However, the proportion of impurities (or as they called in Table 2 "By-products") grows markedly with increased percentages of antimony pentachloride (see FIG. 3).

This observation is significant. On further analysis, a majority of the by-products from the reactions consisted of two stereoisomers of bis-1,2,2,2-tetrafluoroethyl ether. The proportion of this by-product ether in the crude product provides a reliable indicator for judging the efficiency of the particular reaction. Based on the structure of bis-1,2,2,2-tetrafluoroethyl ether it is apparent that two equivalents of desflurane (or isoflurane) are consumed to produce one equivalent of this ether.

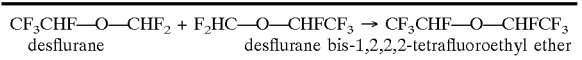

CF$_3$CHF—O—CHF$_2$ + F$_2$HC—O—CHFCF$_3$ → CF$_3$CHF—O—CHFCF$_3$
desflurane                  desflurane bis-1,2,2,2-tetrafluoroethyl ether Although the direct chemical mechanism of the formation of this by-product ether is unknown, it is believed that antimony pentachloride participates in this transformation.

In other words, the increase in "By-products" concentration is achieved at the expense of the formation of desflurane. Suppression of this side-reaction by diminishing the amount of antimony pentachloride in the reaction mixture would increase the amount of desflurane isolated, and reduce the amount of waste generated by the reaction.

In Entry 2 of Table 2 the amount of antimony pentachloride catalyst was decreased 2.25-fold as compared to the reference conditions described in Example 2. This decrease in the amount of catalyst resulted in ~37% decrease in desflurane concentration in the crude product (59.06% vs. 96.55%, compare with Entry 2 of Table 1). At the same time, however, the decrease in antimony pentachloride catalyst led to a more than 12-fold drop in the amount of impurities (0.114% vs. 1.410%, compare with Entry 2 of Table 1) in the crude reaction product. The organic recovery and the yield of the reaction, which employed the decreased amount of catalyst, were comparable with the numbers obtained using the reference conditions. The results obtained for Entry 2 of Table 2 using 0.8 mol. % of the catalyst were judged to be a suitable starting point for further experiments that were designed to evaluate the effect of the proportion of added hydrogen fluoride on the reaction performance.

Example 4

Effect of Varying Proportions of Hydrogen Fluoride on the Reaction Performance

In this experiment, the amount of SbCl$_5$ was maintained at 0.8 mol. %, while the proportion of hydrogen fluoride added to the reaction mixture was increased using the general procedure described in Example 1 in the laboratory-scale Teflon® reactor (250 mL volume). The results of the experiment are shown in Table 3.

TABLE 3

| # | Reagents Iso/HF Molar ratio | SbCl$_5$ mol. % | Des, % | Iso, % | By-products, % | Recovery, % | Conversion, % | Yield, % |
|---|---|---|---|---|---|---|---|---|
| 1 | 1:1.20 | 0.8 | 59.06 | 40.82 | 0.114 | 85.9 | 52.7 | 78.9 |
| 2 | 1:1.44 | 0.8 | 76.87 | 22.93 | 0.207 | 83.0 | 65.3 | 79.4 |
| 3 | 1:1.56 | 0.8 | 88.98 | 10.64 | 0.385 | 82.4 | 74.3 | 80.8 |
| 4 | 1:1.68 | 0.8 | 90.34 | 9.33 | 0.329 | 79.7 | 72.9 | 78.2 |

Figure 4:
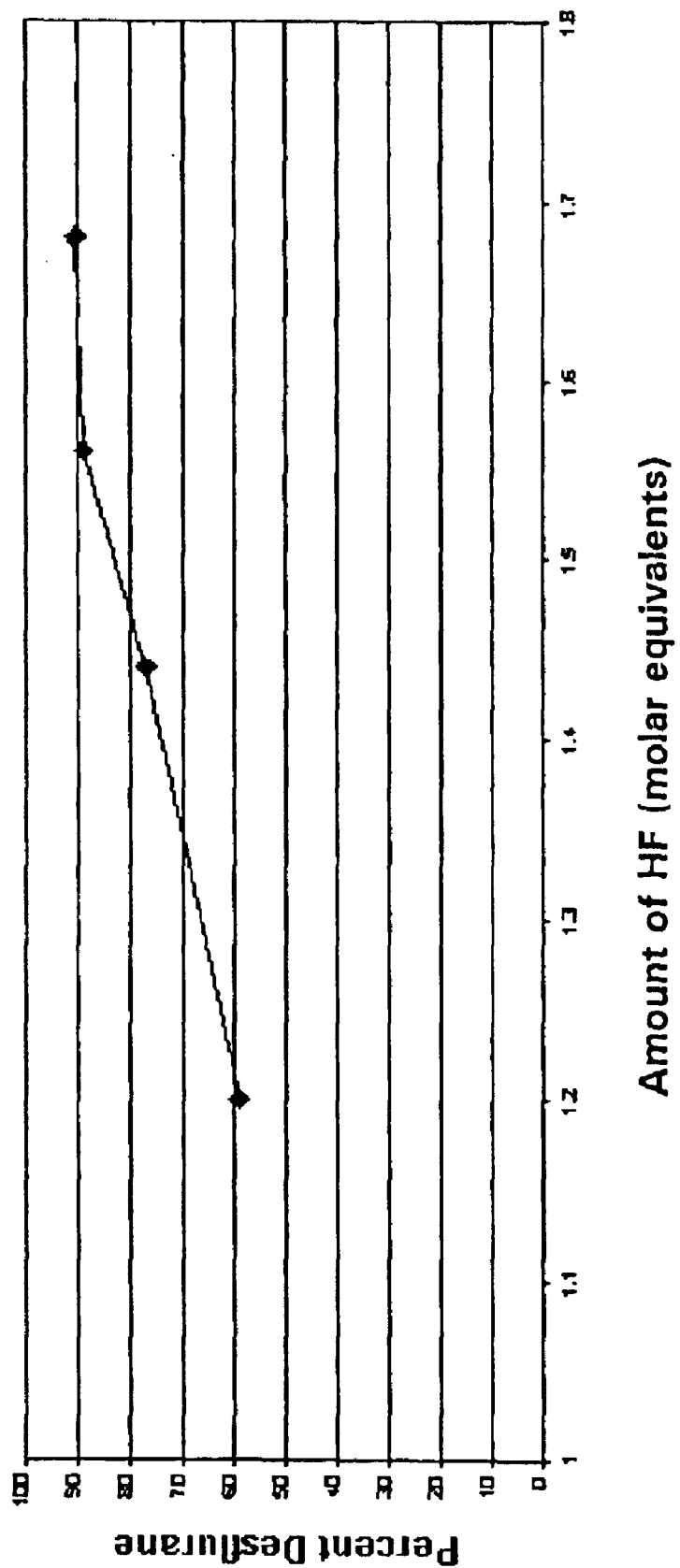
FIG. 4 is a graphical representation of the relationship of the percentage of desflurane present in the crude product and varying molar equivalents of hydrogen fluoride/isoflurane at a constant amount of antimony pentachloride (0.8 mol. %).
Figure 5:
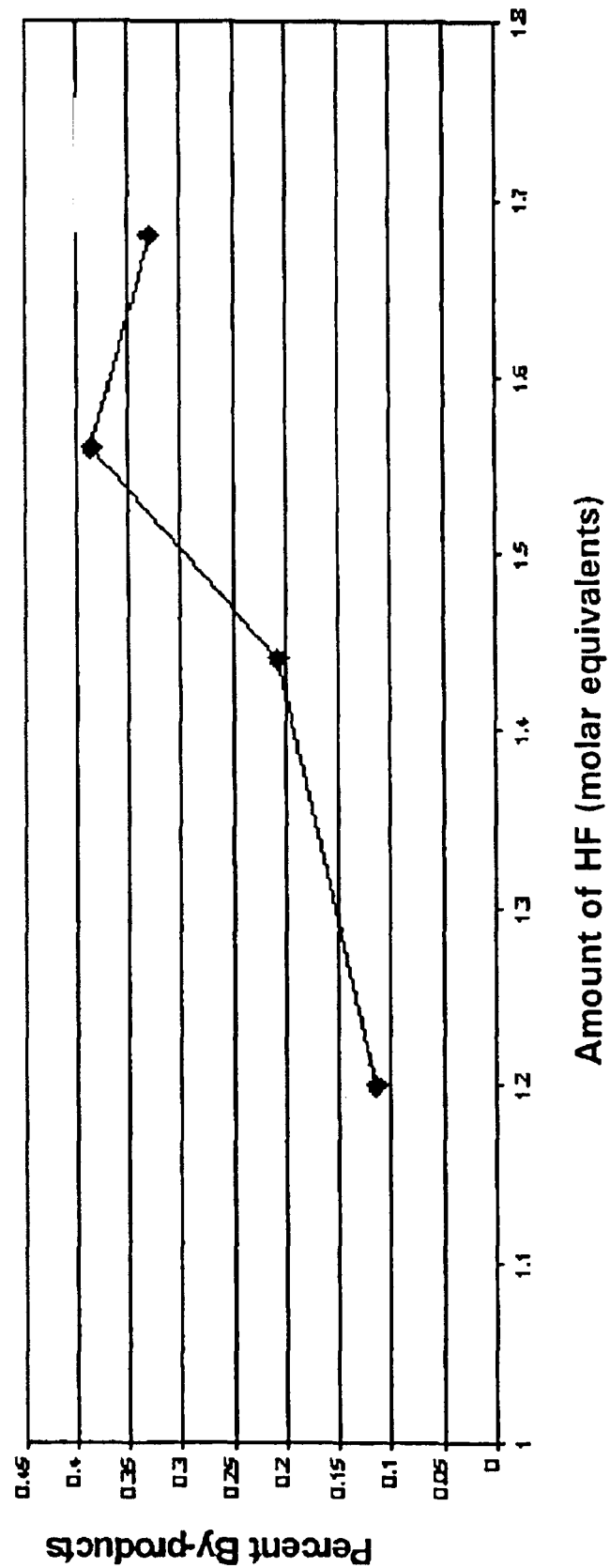
FIG. 5 is a graphical representation of the relationship of the percentage of by-products present in the crude product and varying molar equivalents of hydrogen fluoride/isoflurane at a constant amount of antimony pentachloride (0.8 mol. %).

The data in Table 3 shows that a gradual increase in the amount of hydrogen fluoride added led to increasing concentrations of desflurane in the crude reaction product. Entry 3 of the Table 3 was judged to provide an optimum combination of high desflurane concentration and low by-products concentration. At the same time, the proportions of reagents used in Entry 3 provide good recovery, conversion and yield. FIGS. 4 and 5 further illustrate this observation.

Example 5

Reaction Performance with Optimized Reagent Concentrations in a Carbon Steel Reactor In order to confirm the optimized conditions determined using the laboratory-scale Teflon® reactor, the reaction was run using the new, optimized conditions in the 250-mL reactor made from carbon steel SA-516, Gr.70, which is the material of choice for the commercial-scale fluorination reactors. In Table 4, the results of this study are compared with the results obtained using the reference conditions described in Example 2.

Example 6

Effect of the Length of the Hydrogen Fluoride Post-Addition Period on the Reaction Performance using the Optimized Reagent Ratios We also investigated the influence of the length of the reaction time after the hydrogen fluoride addition was completed ("the post-addition period") on the performance of the reaction in the laboratory-scale carbon steel reactor (250-mL volume) using the optimized reagent ratios. At the end of the indicated post-addition period, the reaction mixture was quenched as described in Example 1. The results of this study are shown in Table 5.

TABLE 4

| | | Reagents | | Products | | | | | |
|---|---|---|---|---|---|---|---|---|---|
| # | Lot | Molar ratio Isoflurane/HF | $SbCl_5$, Mol. % | Des, % | Iso, % | By-products, % | Recovery, % | Conversion, % | Yield, % |
| 1 | Average of 3 runs in new conditions | 1:1.56 | 0.8 | 93.43 | 6.10 | 0.470 | 86.7 | 81.8 | 86.0 |
| 2 | Average of three runs — in reference conditions | 1:1.9 | 1.8 | 96.55 | 2.04 | 1.41 | 78.8 | 77.3 | 78.5 |

TABLE 5

| | Post Addition Period Time, Hrs | Products | | | Recovery, % | Conversion, % | Yield, % |
|---|---|---|---|---|---|---|---|
| # | | Des, % | Iso, % | By-products, % | | | |
| 1 | 5 | 93.90 | 5.72 | 0.382 | 85.6 | 81.1 | 84.9 |
| 2 | 6 | 94.98 | 4.57 | 0.449 | 88.2 | 82.7 | 85.8 |
| 3 | 7 | 94.86 | 4.90 | 0.245 | 86.5 | 82.6 | 85.9 |
| 4 | 8 | 96.61 | 2.90 | 0.490 | 87.1 | 84.8 | 86.8 |

A comparison of the results in Table 4 shows that the results obtained using the optimized conditions are significantly better than those obtained using the reference conditions. Thus, while the concentration of desflurane in the crude reaction product remained practically the same, the concentration of by-product dropped 3 fold. Moreover, the recovery, conversion and yield under the optimized conditions were 7.9%, 4.5%, and 7.5% higher, respectively than those obtained using the reference conditions.

From the data in Table 5 it is apparent that for this particular set of conditions and equipment, the optimum post-addition period was around 6–7 hrs. Further increase of the reaction time was not economically justified since it failed to provide a substantial increase in desflurane concentration.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method for the preparation of desflurane comprising: reacting isoflurane with 0.7–1.2 mol. % of antimony pentachloride and 1.3–2.2 molar equivalents of hydrogen fluoride.

2. The method of claim 1, wherein the reaction is conducted with 1.5–2.0 molar equivalents of hydrogen fluoride.

3. The method of claim 1, wherein the reaction is conducted at temperatures of 9–18° C.

4. The method of claim 1, wherein the reaction is conducted for about 6 to 7 hours after the addition of hydrogen fluoride is completed.

5. The method of claim 1, wherein hydrogen fluoride is added at the rate of 0.25 to 1.5 molar equivalents per hour to a mixture of isoflurane and antimony pentachloride.

* * * * *